US007921020B2

(12) United States Patent
Kalies

(10) Patent No.: US 7,921,020 B2
(45) Date of Patent: Apr. 5, 2011

(54) METHOD FOR GENERATING MEDICAL INTELLIGENCE FROM PATIENT-SPECIFIC DATA

(75) Inventor: Ralph F. Kalies, Picket, WI (US)

(73) Assignee: Omnicare Inc., Covington, KY (US)

( * ) Notice: Subject to any disclaimer, the term of this patent is extended or adjusted under 35 U.S.C. 154(b) by 2170 days.

(21) Appl. No.: 10/756,010

(22) Filed: Jan. 13, 2004

(65) Prior Publication Data

US 2004/0143594 A1    Jul. 22, 2004

Related U.S. Application Data

(60) Provisional application No. 60/439,757, filed on Jan. 13, 2003.

(51) Int. Cl.
*G06Q 10/00* (2006.01)
*G06Q 50/00* (2006.01)

(52) U.S. Cl. ................................. 705/2; 705/3
(58) Field of Classification Search ............. 705/2–3
See application file for complete search history.

(56) References Cited

U.S. PATENT DOCUMENTS

| | | | |
|---|---|---|---|
| 5,371,878 A | 12/1994 | Coker | |
| 6,163,770 A | 12/2000 | Gamble et al. | |
| 6,223,164 B1 | 4/2001 | Seare et al. | |
| 6,304,848 B1 | 10/2001 | Singer | |
| 6,421,650 B1 * | 7/2002 | Goetz et al. | 705/3 |
| 6,654,724 B1 * | 11/2003 | Rubin et al. | 705/3 |
| 7,191,183 B1 * | 3/2007 | Goldstein | 707/101 |
| 7,275,220 B2 * | 9/2007 | Brummel et al. | 715/804 |
| 2001/0049610 A1 * | 12/2001 | Hazumi | 705/3 |
| 2002/0010679 A1 * | 1/2002 | Felsher | 705/51 |
| 2002/0059080 A1 | 5/2002 | Kasirer et al. | |
| 2002/0069202 A1 | 6/2002 | Elwin Deans et al. | |
| 2002/0099568 A1 | 7/2002 | Turner et al. | |
| 2003/0004753 A1 | 1/2003 | Blackshear, Jr. et al. | |
| 2003/0208378 A1 * | 11/2003 | Thangaraj et al. | 705/2 |
| 2004/0078231 A1 * | 4/2004 | Wilkes et al. | 705/2 |

FOREIGN PATENT DOCUMENTS

| | | |
|---|---|---|
| WO | 00/54123 | 9/2000 |
| WO | 01/33936 | 5/2001 |
| WO | 02/19221 | 3/2002 |

* cited by examiner

*Primary Examiner* — Luke Gilligan
*Assistant Examiner* — Kristine K Rapillo
(74) *Attorney, Agent, or Firm* — Ostrolenk Faber LLP

(57) ABSTRACT

A method for compiling, storing and organizing data, and gathering and reporting medical intelligence derived from patient-specific data. A patient's Minimum Data Set ("MDS") data generated by health care facilities are merged with that patient's pharmacy data to create a comprehensive clinical/pharmacological data set for each patient. The data may first be encrypted to ensure patient privacy before being transmitted by the facility to a data repository via an electronic communication network. Upon receipt at the data repository, the data first must pass through a security screen. If the data is determined to be valid and virus-free, it is decrypted as necessary before being added to a data warehouse for use in a wide variety of therapeutic, statistical, and economic analyses. The data may be partially or completely "de-identified" to remove patient-identifying information so as to protect patient privacy.

2 Claims, 1 Drawing Sheet

METHOD FOR GENERATING MEDICAL INTELLIGENCE FROM PATIENT-SPECIFIC DATA

This application claims priority to U.S. provisional application 60/439,757, filed Jan. 13, 2003, the contents of which are hereby incorporated by reference.

FIELD

This invention relates to a method for managing pharmacy and patient data. Specifically, the invention relates to a method for compiling, storing, organizing and using pharmacy and patient data to gather and report medical intelligence using an electronic communication network such as an intranet or the Internet as a communication medium.

BACKGROUND

Regulatory changes by the United States government over the past decade have mandated the collection of information known as the Minimum Data Set ("MDS") for each patient in nursing homes participating in either Medicare or Medicaid programs. The MDS is a standardized assessment instrument consisting of more than 400 items and is used to help identify and quantify a patient's problems, strengths, needs, and preferences so that the patient's quality of life is maintained or enhanced. Assessment items address such areas as activity preferences, indicators of delirium and depression, cognitive functioning, physical functioning, and rehabilitation potential. These data can be of great value to consulting pharmacists and other health care professionals when used for clinical assessment, improvement in clinical practice, and evaluation of outcomes of care.

The MDS is arranged in alphabetic sections. Section "U" of the MDS pertains to patient medications. Information entered in this section includes the names and dosages of all medications ordered within the previous seven days, as-needed drugs such as pain relievers ordered within the past seven days, the method of medicine administration (i.e., oral, intravenous, etc.), frequency of administration, and the amount of medication administered. Unfortunately, most health and human services agencies (such as state-run Medicaid and federally-administered Medicare programs) have not mandated that section "U" information be supplied. As a result, this valuable information is not available for analysis.

Patient-specific medication information combined with patient-specific MDS information is desirable to gather "medical intelligence" regarding a specific patient's care, particularly in the following areas of concern:

Untreated indication—The patient has a medical problem that would benefit from drug therapy but the patient is not receiving medication for that indication.

Improper drug selection—The patient is receiving drug therapy for a medical problem but the medication is not the most effective available.

Subtherapeutic dosage—The patient has medical problem that is being treated with an inadequate dose of the correct medication.

Failure to receive drugs—The patient has a medical problem but is not receiving any medication (e.g., for pharmaceutical, psychological, sociological, or economic reasons).

Overdosage—The patient has a medical problem that is being treated with too much of the correct drug.

Adverse drug reaction—The patient has a medical problem that is the result of an unintended and detrimental adverse drug effect.

Drug interaction—The patient has a medical problem that is the result of a drug-drug, drug-food, or drug-laboratory interaction.

Drug use without indication—The patient is taking a drug without a valid medical reason.

Managed Care Organizations ("MCOs") and nursing homes are examples of health care organizations that desire this medical intelligence. MCOs work to minimize the cost of health care for their subscribers through a variety of means, including volume purchases, quality control, and negotiated fees. MCOs also have a high level of interest in ensuring that patients receive the proper therapeutics in order to achieve the desired outcome while controlling costs. In particular, nursing homes have an interest in prolonging the lives of their residents by providing quality health care and reducing the medical costs resulting from improper drug therapy.

It is desirable that patient-specific MDS information be collected from nursing homes and that patient-specific medicine information be collected from pharmacies and consulting pharmacies. It is further desired that the information be organized in an electronic format and stored in a data repository. This data must be organized in a manner so as to be compliant with existing and future patient privacy regulations such as those found in the U.S. Health Insurance Portability and Accountability Act ("HIPAA"). In particular, 45 C.F.R. Parts 160 and 164 of the Act relate to standards for privacy of individually identifiable health information (the "Privacy Rule"), promulgated by the Department of Health and Human Services (HHS). In part the privacy rule can restrict the acquisition and use of certain types of patient data, particularly individually identifiable health information. It should be noted that "de-identifying" patient data can entail more than merely redacting the patient's name. This is due to the fact that other patient information such as demographics, medical information, and health care facility information could be used in combination to discern the identity of some patients.

It is also desirable to maximize the use of patient data for gathering patient-specific medical intelligence and for statistical analysis of aggregated data while remaining compliant with applicable patient privacy regulations.

Early methods of directly transferring electronic data from remotely located health care facilities to a data repository have a number of limitations. For example, a data repository that relies on dial-in modems requires many telephone lines to support the input and output needs of multiple data sources and data users. A limited number of telephone lines can create a bottleneck for depositing and extracting data. In addition, depending on the quality of the phone lines, the data transmission rate over the phone lines is often slow, increasing the amount of time required to transfer data and increasing the chances for failed transfers of data. The use of an electronic communication network such as an intranet or the Internet overcomes many of these limitations, making them the medium of choice for multi-site operations. Further, electronic communication networks provide worldwide accessibility and the capability of rapidly transferring data analyses and reports between a large number of locations. However, the open and accessible architecture of many electronic networks such as the Internet makes them a significant security risk. It is undesirable for sensitive patient-related data to be accessed by unauthorized personnel. This can result in the altering or theft of patient data or the dissemination of confidential information to the public or to competitors.

Thus, there is a need for a method to securely accumulate a patient's MDS and drug regimen data, verify it, store it, organize it, and gather medical intelligence by only authorized personnel in a useful format on a timely and secured basis. There is also a need to prevent unauthorized users from altering or viewing the data. There is a further need to provide de-identification of patient data.

SUMMARY

According to the present invention, a method is disclosed for accumulating, storing and organizing data, and gathering and reporting medical intelligence derived from patient-specific data. A patient's MDS data generated by health care facilities are merged with that patient's pharmacy data to create a comprehensive clinical/pharmacological data set for each patient. The data may first be encrypted to ensure patient privacy and then transmitted by the facility regularly, such as daily, to a data repository via an electronic communication network such as an intranet or the Internet.

Upon receipt at the data repository, the encrypted data first must pass through a security screen. If the data is determined to be valid and virus-free, it is then decrypted as necessary before being stored in a "data warehouse." A data warehouse is an electronic database wherein large quantities of related data from many operational systems is merged into a single secure database to provide an integrated information view based on logical queries. The data warehouse is a valuable resource whose data can be analyzed to provide patient-specific information for use in a wide variety of therapeutic, statistical, research, and economic analyses. These analyses can aid the MCO medical and business staffs and other healthcare providers in making timely health care clinical treatment and business related decisions. Analysis of the data warehouse can also provide feedback regarding the impact of prior decisions regarding whether a specific patient or a related class of patients to facilitate improvements in patient care and operational efficiency, and reduce the cost of medical care.

Authorized users may access the data at any time via the electronic communication network to gather medical intelligence and create reports based on relatively current data. To access the stored data, the user first sends a query to the data repository for access. For security purposes, the system may require entry of a username and password. A "digital signature" or "digital certificate" may also be required to authenticate the user's identity. A digital signature is an electronic signature that can be used to authenticate the identity of the sender of a message or the signer of a document. It can also be used to ensure that the original content of the message or document sent is unchanged. A digital certificate is an electronic "passport" issued by a third party that establishes a user's credentials when doing business or making transactions on networks such as the Internet. Once authorization has been verified, access to the data warehouse is granted and the user is able to obtain various types of information residing within the data warehouse. The amount and types of data available for access by any particular user is preferably limited by the user's predetermined security level clearance. The medical intelligence may be presented to the user in a variety of pre-determined report formats as established by the type of data and the job function of the user. The data may be partially or completely "de-identified" to remove patient-identifying information so as to protect patient privacy.

An object of the present invention is a method of generating medical intelligence. Information relating to at least one pharmaceutical transaction is compiled for a specific patient occurring in at least one pharmacy. The patient-specific pharmaceutical transaction information is transmitted to a data repository. Patient information relating to at least one specific patient is also compiled and transmitted to the data repository. The patient-specific pharmaceutical transaction information and specific patient information is stored and organized in a data warehouse. A user defined query is transmitted to the data repository. The patient-specific pharmaceutical transaction information and specific patient information stored in the data warehouse is collected in response to the query. The collected information is arranged into a report having a predetermined format and medical intelligence is derived. The report is transmitted from the data repository to the user. The report comprises patient-specific medical intelligence relating to at least a portion of the compiled patient-specific pharmaceutical transaction information and the specific patient information.

Another object of the present invention is another method of generating medical intelligence. Information relating to at least one pharmaceutical transaction for a specific patient occurring in at least one pharmacy is compiled and transmitted to a data repository. Information relating to at least one specific patient is also compiled and transmitted to the data repository. A security screening of at least one of the patient-specific pharmaceutical transaction information and specific patient information is performed upon receipt at the data repository. Only the patient-specific pharmaceutical transaction information and specific patient information that meets predetermined security screening criteria are accepted. The patient-specific pharmaceutical transaction information and specific patient information are stored and organized in a data warehouse. A user defined query is transmitted to the data repository. The identity of the user is verified in accordance with predetermined verification criteria and the query is accepted only if the identity of the user complies with the verification criteria. The query is compared to predetermined security-level screening criteria and accepted only if the security level of the user complies with the security-level screening criteria. The patient-specific pharmaceutical transaction information and specific patient information stored in the data warehouse is collected in response to the query. The medical intelligence is arranged into a report having a predetermined format medical intelligence is derived. The report is transmitted from the data repository to the user. The report comprises patient-specific medical intelligence relating to at least a portion of the compiled patient-specific pharmaceutical transaction information and the specific patient information.

Still another object of the present invention is yet another method of generating medical intelligence. Information relating to at least one pharmaceutical transaction for a specific patient occurring in at least one pharmacy is compiled and transmitted to a data repository. Patient information relating to at least one specific patient is also compiled and transmitted to the data repository. The patient specific pharmaceutical transaction information and specific patient information is stored and organized in a data warehouse. Patient-specific pharmaceutical transaction information and specific patient information is periodically extracted. The extracted information is analyzed in accordance with a predetermined set of algorithms and rules to derive medical intelligence relating to medications being consumed by the specific patient. The medical intelligence is arranged into a report having a predetermined format and transmitted from the data repository to at least one of a predetermined health care provider and the specific patient. The report comprises at least one recommended treatment protocol corresponding to the medical intelligence.

Yet another object of the present invention is another method of generating medical intelligence. Information relating to a plurality of pharmaceutical transactions occurring in at least one pharmacy is compiled and transmitted to a data repository. Patient information relating to a plurality of patients is also compiled and transmitted to the data repository. Corresponding patient information and pharmaceutical transaction information are stored and organized in a data warehouse. A user defined query is transmitted to the data repository, the query relating to at least a plurality of the patients. The pharmaceutical transaction information and patient information stored in the data warehouse is collected in accordance with the query. The collected information is arranged into a report having a predetermined format and medical intelligence is derived. The report is transmitted from the data repository to the user. The report comprises medical intelligence relating to the compiled pharmaceutical transaction information and the patient information of a plurality of patients.

Another object of the present invention is a method of generating medical intelligence. Information relating to a plurality of pharmaceutical transactions occurring in at least one pharmacy is compiled and transmitted to a data repository. Patient information relating to a plurality of patients is also compiled and transmitted to the data repository. A security screening of at least one of the pharmaceutical transaction information and patient information is performed upon receipt at the data repository. Only pharmaceutical transaction information and patient information that meets predetermined security screening criteria is accepted. Corresponding patient information and pharmaceutical transaction information are stored and organized in a data warehouse. A user defined query is transmitted to the data repository, the query relating to at least a plurality of the patients. The identity of the user is verified in accordance with predetermined verification criteria. The query is accepted only if the identity of the user complies with the verification criteria. The query is compared to predetermined security-level screening criteria and accepted only if the security level of the user complies with the security-level screening criteria. An accepted query is responded to by gathering pharmaceutical transaction information and patient information stored in the data warehouse. The collected information is arranged into a report having a predetermined format medical intelligence is derived. The report is transmitted from the data repository to the user. The report comprises medical intelligence relating to at least a portion of the compiled pharmaceutical transaction information and the patient information.

BRIEF DESCRIPTION OF THE DRAWING

Further features of the inventive embodiments will become apparent to those skilled in the art to which the embodiments relate from reading the specification and claims with reference to the accompanying drawing, in which

DETAILED DESCRIPTION

Figure 1:
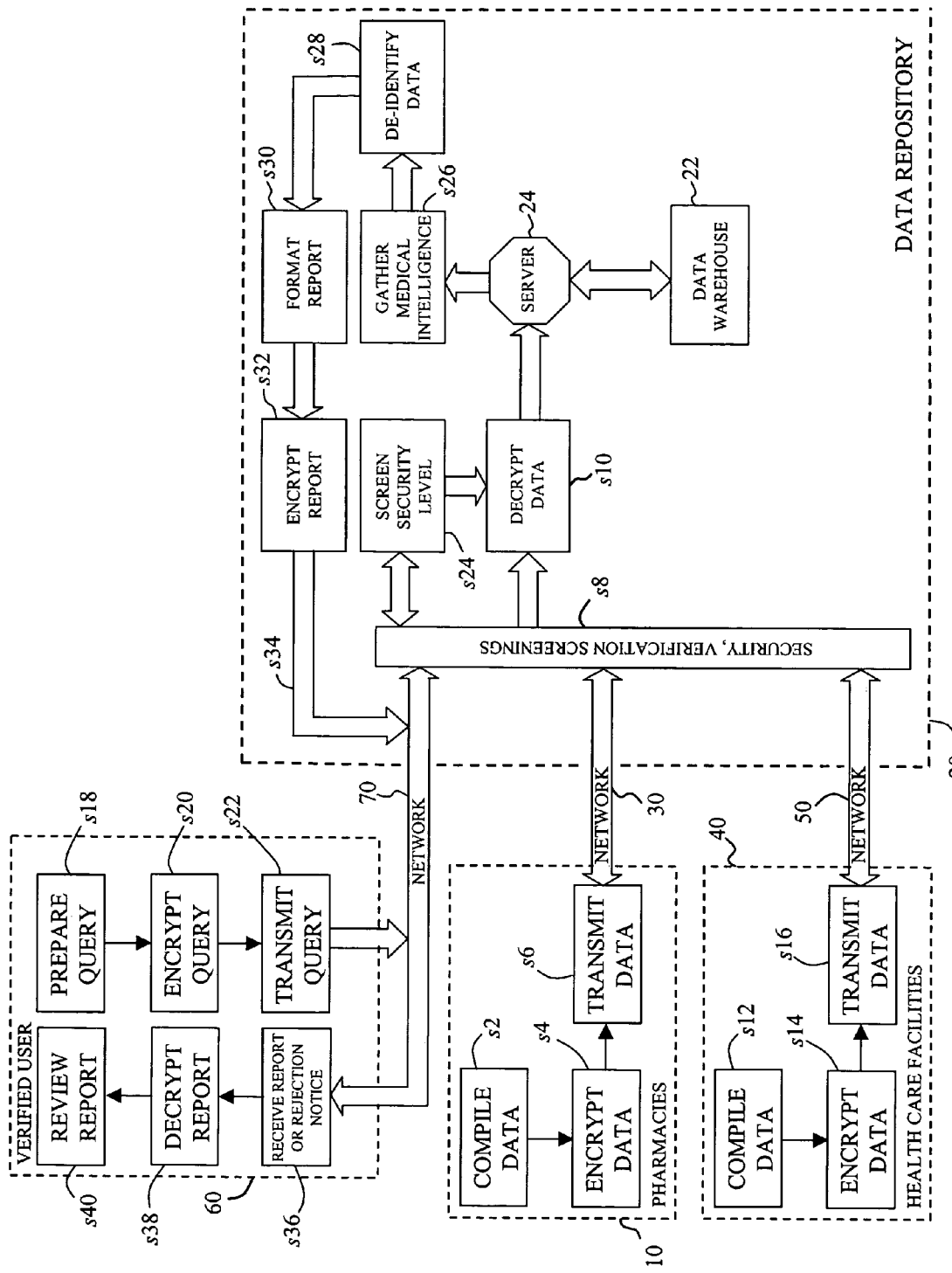
FIG. 1 is a block diagram of a method for accumulating, storing and organizing data, and gathering and reporting medical intelligence derived from patient-specific data according to an embodiment of the present invention.

A block diagram of a method for compiling, storing and reporting medical intelligence is shown in FIG. 1. Pharmacies 10 within an MCO or other health care network compile medical, financial, and other information for pharmaceutical transactions relating to specific patients at step s2, encrypt the information at step s4, and transmit the information at step s6 to a data repository 20 at a remote site. Any conventional encryption method may be used. Example encryption methods include, without limitation, encryption methods based on the Data Encryption Standard ("DES") promulgated by the National Institute of Standards and Technology and Netscape's Secure Sockets Layer ("SSL"). The information is transmitted via an electronic communication network link 30. Type of electronic communication networks include, without limitation, wired and wireless connections to digital data buses, intranets and the Internet.

When the patient-specific pharmaceutical transaction data is received at the data repository 20, the data is subjected to a security screening according to predetermined security screening criteria at step s8. The security screening criteria may include, without limitation, verification of the data source, a validity check, and a check for computer viruses. If the data fails to comply with the predetermined security screening criteria, it is rejected and either returned to the sender via electronic communication network link 30 or discarded. A rejection notice may likewise be sent to the sender of the data via electronic communication network link 30. If the data complies with the predetermined security screening criteria it is deemed acceptable. The accepted data is then decrypted at step s10 and forwarded to a data warehouse 22 by a server 24 for storage and organization in a predetermined conventional logical manner for later retrieval and use.

Likewise, health care facilities 40 within an MCO, nursing home facilities, or other health care network may compile patient information or data which may include, without limitation, clinical data, MDS data, and demographic data for specific patients at step s12, encrypt the data at step s14, and then transmit the data to the data repository 20 at step s16 via an electronic communication network link 50. This data is also subjected to a security screening at step s8 in accordance with predetermined security screening criteria. The security screening criteria may include, without limitation, verification of the data source, a validity check, and a check for computer viruses. If the MDS data fails to comply with the predetermined security screening criteria, it is rejected and either returned to the sender via electronic communication network link 50 or discarded. A rejection notice may likewise be sent to the sender of the data via electronic communication network link 50. If the MDS data complies with the predetermined security screening criteria it is deemed acceptable. The accepted data is then decrypted at step s10 and forwarded to a data warehouse 22 by a server 24 for storage and organization in a predetermined conventional logical manner for later retrieval and use.

In one embodiment of the present invention, accepted pharmacy transaction data and MDS data for a specific patient are organized such that they are logically linked or related to each other within the data warehouse, together forming an comprehensive clinical and pharmacological data set for the patient. The logical relationship may be established when the data is stored and organized. Alternatively, the logical relationship may be established when data is retrieved and assembled in response to a query. Queries are discussed in greater detail below.

After the MDS and patient medicine information are stored in data warehouse 22, the patient-specific MDS and pharmacy information are organized by being logically linked and related by the data warehouse 22 to facilitate subsequent queries. A query is a structured method of defining and relating a portion of a set of data so as to retrieve relevant information from a data warehouse that is organized in a predetermined manner. The organization of the data that is retrieved may also be defined by the query. For example, a query might be prepared to retrieve a listing of all antidepressants given to a specific patient during a specified range of time, listed chronologically.

A user 60 may access the data repository 20 at any time and from any location via an electronic communication network link 70. User 60 prepares and transmits an encrypted query to the data repository 20 at steps s18,s20,s22 via the electronic communication network link 70. To restrict access to the data repository 20 to only authorized users 60, a predetermined query structure, established by the data repository, may include a requirement that user verification data also be provided. The user verification data may be subjected to a verification screening at step s8 in accordance with predetermined criteria such as an assigned username and password or via any conventional biometric means such as, without limitation, fingerprints and retinal scans. Conventional digital signatures and/or digital certificates may also be used to verify the user at step s8. An example digital signature standard is the Digital Signature Standard ("DSS") established by the NIST. An example digital certificate standard is the ITU-T X509 international standard established by the International Telecommunications Union (ITU). If the user does not satisfy the verification criteria, a query rejection notice may be sent to the user via electronic communication network link 70. A copy of the rejection notice may also be sent to predetermined security personnel for tracking and possible investigation as an attempted security breach.

Once the identity of the user 60 is verified in accordance with the verification screening criteria, the query is accepted and forwarded to an internal security-level screening at step s24. To protect patient privacy, the security-level screening s24 determines what information from the data warehouse 22 may be made available to a specific user 60, based on that user's predetermined data and security level. For example, if the username and password identify the user 60 as a clinical pharmacist for a health care facility, user 60 may be limited to accessing information only relating to patients at that specific facility. However, if the username and password identify user 60 as a regional-level clinical pharmacist responsible for several health care facilities, the user may have access to information for all patients in those facilities. Thus, a predetermined hierarchy is established which defines the extent to which a particular verified user may access information, such that the verified user's username and password are assigned separately or in combination to a particular access level within the hierarchy.

If verified user 60 attempts to access data that is beyond the user's predetermined security level, a query rejection notice may be sent to the user via electronic communication network link 70. A copy of the rejection notice may also be sent to predetermined security personnel for tracking and possible investigation as an attempted security breach. If, based on the security-level screening at step s24, user 60 is determined to have a valid need-to-know requirement for the information requested in the query the query is accepted and then forwarded to data warehouse 22 by server 24. Data relevant to the query is extracted in response to the query is output to the server 24 by data warehouse 22, and may be gathered and organized into medical intelligence at step s26. Medical intelligence may be generally defined as data that has been accumulated, compiled and analyzed according to at least one result-specific algorithm to determine relationships between patients, maladies, treatments and outcomes in an effort to improve subsequent outcomes. Medical intelligence may be based on predetermined metrics, rules and algorithms that facilitate review and analysis of the data in accordance with accepted medical and pharmacological practices and standards. The organized medical intelligence may further comprise the establishment of a logical relationship or link between pharmacy transaction data and patient-specific information, such as MDS data, thus forming an comprehensive clinical and pharmacological data set for a specific patient.

Depending upon the security level of user 60 and the type of query, some or all of the medical intelligence may be de-identified at step s28 to protect patient privacy. In general, the medical intelligence may be considered to be de-identified when some or all of the following patient information has been removed: name; all geographic subdivisions smaller than a state; complete zip code or equivalents; dates directly related to the patient, ages over 89 or dates indicating such an age; telephone number; fax number; email address; social security number; medical record number; health plan number; account numbers; certificate or license numbers; vehicle identification/serial numbers, including license plate numbers; device identification/serial numbers; Universal Resource Locators (URLs); Internet Protocol (IP) addresses; biometric identifiers; full face photographs and comparable images; and any other unique identifying number, characteristic or code. It is important to note that this list is not exhaustive or complete, and is intended for illustrative purposes only.

The medical intelligence is arranged at step s30 to a predetermined format based on the needs of user 60 and their security clearance level. The formatted report, which may be based on current data, is preferably encrypted at step s32 and then transmitted to user 60 at step s34 via the electronic communication network link 70. User 60 receives the report at step s36, which is then decrypted at step s38, and made available for the user at step s40.

A variety of reports containing derived medical intelligence may be obtained regarding a specific patient's medications and the therapeutic effect of previously prescribed medications as determined by analysis of the pharmacy data for the patient in combination with the patient's medical condition as reflected in the MDS. For example, inquiries may be made to check for possible mis-medication conditions such as untreated conditions, improper drug selection, sub-therapeutic dosage, failure to receive drugs, overdosage, adverse drug reaction, drug interaction, and drug use without indication. Reports may indicate a patient's condition at a given point in time, or may provide trend information such as responses to medications and changes in medications over a period of time.

In an alternate embodiment of the present invention, data warehouse 22 may additionally be organized using algorithms and rules to facilitate automatic monitoring and querying of a patient's medications, history, and MDS data, and to automatically provide the patient's health care providers with alerts if any issues or concerns are detected. In the following discussion, it is to be understood that the steps of FIG. 1 that are not specifically discussed may be used in this embodiment in the same manner as previously disclosed. With continued reference to FIG. 1, data warehouse 22 may be programmed to periodically extract a patient's MDS and pharmacy data to gather medical intelligence at step s26. The patient-specific pharmaceutical transaction information and a patient's clinical information is analyzed in accordance with a predetermined set of algorithms and rules to obtain medical intelligence relating to potential problems or protocols for improved treatment associated with medications being consumed by the specific patient. For example, the medical intelligence may check for any adverse results that may be tied to the medications the patient is receiving and consuming. If a potential problem is detected, data repository 20 will automatically issue an alerting report, which is formatted at step s30, encrypted at step s32, and transmitted to user 60 at step s34 via the electronic communication network 70. In this embodiment user 60 may be at least one of the patient, the patient's health care providers, and the facility responsible for the care of the patient. User 60 receives the report at step s36, decrypts the report at step s38, and reviews the report at step s40. The report may then be used to alter the patient's medications to alleviate the concerns or implement the improved treatment protocol noted in the report issued from the data repository 20.

An example scenario is a situation where a patient's MDS indicates that the patient's physical functioning has been reduced subsequent to a change in medication. Data repository 20 may include a monitoring function wherein the patient's data is routinely extracted from data warehouse 22, and organized at step s26. The rules and algorithms of step s26 may detect the change in the patient's condition, review the patient's medication records, and determine that the patient's new medication, acting in combination with other medications, could be causing an adverse reaction. The data repository 20, performing this analysis through an automated and regular review of the patient's MDS and pharmacy records, may then issue a report noting the change in the patient's condition and suggesting alternative treatment. The report is formatted at step s30, encrypted at step s32, and then automatically sent to the responsible health care providers 60 at step s34 via electronic communications link 70. The data repository 20 may also analyze the patient's clinical MDS data in a trend format to provide early feedback as to the efficacy of any changes in treatment. This can provide the health care provider user 60 with regular cause-and-effect information feedback so that additional changes in treatment may be implemented if indicated, depending upon the patient's response.

In another alternate embodiment, the patient-specific data may be aggregated to perform statistical analyses on the patient population as a whole. Such statistical analyses may include reviews of the efficacy and side effects of particular medications, "top ten" analyses of medications, symptoms and ailments, and studies based on patient demographics. In the following discussion, it is to be understood that the steps of FIG. 1 that are not specifically discussed may be used in this embodiment in the same manner as previously disclosed. With continued reference to FIG. 1, in this embodiment a user 60, such as a clinical researcher having a system-wide security clearance, issues a query to the data repository 20 at step s18 via a network 70, utilizing the previously discussed encryption step s20, transmission step s22, and security screening step s8. The query is passed to the data warehouse 22, which extracts patient-population-wide data pertinent to the query. Medical intelligence is gathered at step s26 using the extracted patient-population data. The data is de-identified at step s28 to protect patient privacy, formatted into a report at step s30, encrypted at step s32, then sent to user 60 at step s34 via electronic communication network 70. User 60 receives the report at step s36, where it is decrypted at step s38, and made available for review at step s40.

The present invention provides a number of improvements in health care. First and foremost, patients benefit from the continuous optimization of the types and amounts of medicines that are administered, maximizing the efficacy of the treatments and in many cases, thus improving the patient's quality of life. The present invention also supplies health care providers with feedback regarding adverse changes in the patient's condition that may be linked to certain medications.

Further, the present invention can ensure that the health care facility is in compliance with standards established by regulatory agencies and periodically verified via audits. Lastly, by ensuring that the patients are provided with optimized types and amounts of medications, health care organizations such as MCOs can provide quality health care while controlling costs.

While this invention has been shown and described with respect to a detailed embodiment thereof, it will be understood by those skilled in the art that various changes in form and detail thereof may be made without departing from the scope of the claims of the invention.

What is claimed is:

1. A method for using a computer to generate medical intelligence to enable improved medical treatment of a patient, comprising:

receiving electronic pharmacy transaction information at an electronic data warehouse from a pharmacy computer, wherein the electronic pharmacy transaction information relates to a pharmaceutical transaction that identifies a medication being used by the patient;

receiving electronic patient specific information at the electronic data warehouse from a computer other than the pharmacy computer, wherein the electronic patient specific information includes information concerning the patient's physical condition;

merging the electronic pharmacy transaction information and the electronic patient specific information in the electronic data warehouse and associating the electronic patient specific information with the electronic pharmacy transaction information to generate merged information wherein the electronic patient specific information and the electronic pharmacy transaction information are associated with each other to provide medical intelligence relating to medications being consumed by the specific patient;

analyzing with a computer processor the merged information in accordance with predetermined algorithms to generate the medical intelligence, wherein the medical intelligence relates to potential problems or protocols for improved treatment associated with the medication being used by the patient; and electronically generating a report to alert a responsible person of the potential problem or protocol for improved treatment;

further comprising aggregating the electronic patient specific information for a plurality of patients and using the processor to perform a statistical analysis on the plurality of patients as a population as a whole to determine efficacy or side effects of medication being used by the patient population as a whole.

2. The method of claim 1, wherein the electronic patient specific information indicates that the patient's physical functioning has been reduced subsequent to the medication used by the patient;

further wherein the step of analyzing further includes monitoring the patient specific information to detect a change in the patient's condition and determining that the change in condition is potentially caused by the medication; and further wherein the report alerts the responsible person that an alternative treatment is potentially necessary.

* * * * *